United States Patent
Birk

(10) Patent No.: US 8,900,117 B2
(45) Date of Patent: Dec. 2, 2014

(54) RELEASABLY-SECURABLE ONE-PIECE ADJUSTABLE GASTRIC BAND

(75) Inventor: Janel A. Birk, Oxnard, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 1899 days.

(21) Appl. No.: 10/587,099

(22) PCT Filed: Jan. 21, 2005

(86) PCT No.: PCT/US2005/001620
§ 371 (c)(1),
(2), (4) Date: Dec. 4, 2008

(87) PCT Pub. No.: WO2005/072195
PCT Pub. Date: Aug. 11, 2005

(65) Prior Publication Data
US 2009/0082793 A1    Mar. 26, 2009

Related U.S. Application Data

(60) Provisional application No. 60/538,595, filed on Jan. 23, 2004.

(51) Int. Cl.
*A61F 2/00* (2006.01)
*A61B 17/08* (2006.01)
*A61F 5/00* (2006.01)
*A61B 17/132* (2006.01)
*A61B 17/135* (2006.01)

(52) U.S. Cl.
CPC ............... *A61F 5/0066* (2013.01); *A61F 5/003* (2013.01); *A61F 5/0056* (2013.01); *A61B 17/1327* (2013.01); *A61B 17/135* (2013.01)
USPC ............................................. 600/37; 606/151

(58) Field of Classification Search
USPC ............. 606/151, 157, 153; 600/37; 604/909; 24/16 PB, 17 A, 17 B, 17 AP, 771
See application file for complete search history.

(56) References Cited

U.S. PATENT DOCUMENTS

| | | |
|---|---|---|
| 1,174,814 A | 3/1916 | Brennan et al. |
| 1,830,947 A | 11/1931 | Klingel |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Helioscopie Product Insert for *Heliogast*, pp. 1-11 (undated).

(Continued)

*Primary Examiner* — Julian W Woo
(74) *Attorney, Agent, or Firm* — Gordan & Jacobson, PC

(57) ABSTRACT

A releasably-securable gastric band (12) having a tail end (10a) and a head end (10b) for receiving the tail end (10a) is disclosed. The gastric band (12) also includes a releasable locking means (20) that releasably secures the head (10b) and tail ends (10a) together. The tail end (10a) may include a tooth (14) and the head end (10b) may include a notch (22) for engaging the tooth (14). Upon insertion of the tail end (10a) into the head end (10b), the tooth (14) mates with the notch (22) and releasably locks the tail end (10a) in the head end (10b). The releasably-securable gastric band (12) includes a release tab (24). When force is applied to the release tab (24) in a direction perpendicular to a central axis of the gastric band (12), the tooth (14) is disengaged from the notch (22) to allow the gastric band (12) to be released.

17 Claims, 4 Drawing Sheets

(56) References Cited

U.S. PATENT DOCUMENTS

| | | | |
|---|---|---|---|
| 1,999,683 | A | 4/1935 | Borresen |
| 2,163,048 | A | 6/1939 | McKee |
| 2,339,138 | A | 1/1944 | Black |
| 2,405,667 | A | 8/1946 | Ottesen |
| 2,438,231 | A | 3/1948 | Schultz et al. |
| 2,635,907 | A | 4/1953 | Heimbuch |
| 2,714,469 | A | 8/1955 | Carlson |
| 2,936,980 | A | 5/1960 | Rapata |
| 3,059,645 | A | 10/1962 | Hasbrouck et al. |
| 3,189,961 | A | 6/1965 | Heller |
| 3,340,083 | A | 9/1967 | Cummins |
| 3,667,081 | A | 6/1972 | Burger |
| 3,840,018 | A | 10/1974 | Heifetz |
| 3,955,834 | A | 5/1976 | Ahlrot |
| 4,053,176 | A | 10/1977 | Hilbush |
| 4,118,805 | A | 10/1978 | Reimels |
| 4,133,315 | A | 1/1979 | Berman et al. |
| 4,157,713 | A | 6/1979 | Clarey |
| 4,176,412 | A | 12/1979 | Peterson |
| 4,236,521 | A | 12/1980 | Lauterjung |
| 4,271,827 | A | 6/1981 | Angelchik |
| 4,299,012 | A | 11/1981 | Oetiker |
| 4,399,809 | A | 8/1983 | Baro et al. |
| 4,408,597 | A | 10/1983 | Tenney, Jr. et al. |
| 4,417,567 | A | 11/1983 | Trick |
| 4,424,208 | A | 1/1984 | Wallace et al. |
| 4,442,153 | A | 4/1984 | Meltsch |
| 4,450,375 | A | 5/1984 | Siegal |
| 4,485,805 | A | 12/1984 | Foster, Jr. |
| 4,492,004 | A | 1/1985 | Oetiker |
| 4,551,862 | A | 11/1985 | Haber |
| 4,558,699 | A | 12/1985 | Bashour |
| 4,559,699 | A | 12/1985 | Owen et al. |
| 4,582,640 | A | 4/1986 | Smestad et al. |
| 4,582,865 | A | 4/1986 | Balazs et al. |
| 4,592,339 | A * | 6/1986 | Kuzmak et al. ............. 128/899 |
| 4,592,355 | A | 6/1986 | Antebi |
| 4,601,713 | A | 7/1986 | Fuqua |
| 4,631,782 | A * | 12/1986 | Gecs ............................ 24/16 PB |
| 4,667,672 | A | 5/1987 | Romanowski |
| 4,671,351 | A | 6/1987 | Rappe |
| 4,693,695 | A | 9/1987 | Cheng |
| 4,694,827 | A | 9/1987 | Weiner et al. |
| 4,696,288 | A | 9/1987 | Kuzmak et al. |
| 4,708,140 | A | 11/1987 | Baron |
| 4,716,154 | A | 12/1987 | Malson et al. |
| 4,753,086 | A | 6/1988 | Schmidt |
| 4,760,837 | A | 8/1988 | Petit |
| 4,803,075 | A | 2/1989 | Wallace et al. |
| 4,881,939 | A | 11/1989 | Newman |
| 4,883,467 | A | 11/1989 | Franetzki et al. |
| 4,886,787 | A | 12/1989 | de Belder et al. |
| 4,896,787 | A | 1/1990 | Delamour et al. |
| 4,915,690 | A | 4/1990 | Cone et al. |
| 4,925,446 | A | 5/1990 | Garay et al. |
| 4,944,487 | A | 7/1990 | Holtermann |
| 4,944,659 | A | 7/1990 | Labbe et al. |
| 4,958,791 | A * | 9/1990 | Nakamura ................... 248/74.1 |
| 4,969,899 | A | 11/1990 | Cox, Jr. |
| 4,994,019 | A | 2/1991 | Fernandez et al. |
| 5,031,943 | A * | 7/1991 | Scott et al. ................. 24/16 PB |
| 5,045,060 | A | 9/1991 | Melsky et al. |
| 5,074,868 | A | 12/1991 | Kuzmak |
| 5,084,061 | A | 1/1992 | Gau et al. |
| 5,091,171 | A | 2/1992 | Yu et al. |
| 5,116,652 | A | 5/1992 | Alzner |
| 5,120,313 | A | 6/1992 | Elftman |
| 5,143,724 | A | 9/1992 | Leshchiner et al. |
| 5,152,770 | A | 10/1992 | Bengmark et al. |
| 5,160,338 | A | 11/1992 | Vincent |
| 5,188,609 | A | 2/1993 | Bayless et al. |
| 5,224,494 | A | 7/1993 | Enhorning |
| 5,226,429 | A | 7/1993 | Kuzmak |
| 5,246,456 | A | 9/1993 | Wilkinson |
| 5,246,698 | A | 9/1993 | Leshchiner et al. |
| 5,259,399 | A | 11/1993 | Brown |
| 5,326,349 | A | 7/1994 | Baraff |
| 5,343,894 | A | 9/1994 | Frisch et al. |
| 5,356,883 | A | 10/1994 | Kuo et al. |
| 5,360,445 | A | 11/1994 | Goldowsky |
| 5,391,156 | A | 2/1995 | Hildwein et al. |
| 5,399,351 | A | 3/1995 | Leshchiner et al. |
| 5,449,363 | A | 9/1995 | Brust et al. |
| 5,449,368 | A | 9/1995 | Kuzmak |
| 5,458,568 | A | 10/1995 | Racchini et al. |
| 5,509,888 | A | 4/1996 | Miller |
| 5,531,716 | A | 7/1996 | Luzio et al. |
| 5,535,752 | A | 7/1996 | Halperin et al. |
| 5,554,113 | A | 9/1996 | Novak et al. |
| 5,562,714 | A | 10/1996 | Grevious |
| 5,601,604 | A * | 2/1997 | Vincent ........................ 606/216 |
| 5,607,418 | A | 3/1997 | Arzbaecher |
| 5,633,001 | A | 5/1997 | .ANG.gerup |
| 5,653,718 | A | 8/1997 | Yoon |
| 5,658,298 | A | 8/1997 | Vincent et al. |
| 5,676,162 | A | 10/1997 | Larson, Jr. et al. |
| 5,695,504 | A | 12/1997 | Gifford, III et al. |
| 5,704,097 | A * | 1/1998 | Rahav ........................ 24/16 PB |
| 5,704,893 | A | 1/1998 | Timm |
| 5,713,911 | A | 2/1998 | Racenet et al. |
| 5,733,257 | A | 3/1998 | Sternby |
| 5,748,200 | A | 5/1998 | Funahashi |
| 5,766,218 | A * | 6/1998 | Arnott ........................ 606/151 |
| 5,766,232 | A | 6/1998 | Grevious et al. |
| 5,769,877 | A | 6/1998 | Barreras, Sr. |
| 5,785,295 | A | 7/1998 | Tsai |
| 5,817,113 | A | 10/1998 | Gifford, III et al. |
| 5,827,529 | A | 10/1998 | Ono et al. |
| 5,833,698 | A | 11/1998 | Hinchliffe et al. |
| 5,861,014 | A | 1/1999 | Familoni |
| RE36,176 | E | 3/1999 | Kuzmak |
| 5,886,042 | A | 3/1999 | Yu et al. |
| 5,904,697 | A | 5/1999 | Gifford, III et al. |
| 5,910,149 | A | 6/1999 | Kuzmak |
| 5,928,195 | A | 7/1999 | Malamud et al. |
| 5,938,669 | A | 8/1999 | Klaiber et al. |
| 5,944,696 | A | 8/1999 | Bayless et al. |
| 5,944,751 | A | 8/1999 | Laub |
| 5,993,473 | A | 11/1999 | Chan et al. |
| 6,003,208 | A * | 12/1999 | Christian et al. ............ 24/16 PB |
| 6,013,679 | A | 1/2000 | Kuo et al. |
| 6,024,340 | A | 2/2000 | Lazarus et al. |
| 6,024,704 | A | 2/2000 | Meador et al. |
| 6,048,309 | A | 4/2000 | Flom et al. |
| 6,067,991 | A | 5/2000 | Forsell |
| 6,074,341 | A | 6/2000 | Anderson et al. |
| 6,074,378 | A | 6/2000 | Mouri et al. |
| 6,083,249 | A | 7/2000 | Familoni |
| 6,090,131 | A | 7/2000 | Daley |
| 6,102,678 | A | 8/2000 | Peclat |
| 6,102,922 | A | 8/2000 | Jakobsson et al. |
| 6,171,321 | B1 | 1/2001 | Gifford, III et al. |
| 6,193,734 | B1 | 2/2001 | Bolduc et al. |
| 6,203,523 | B1 | 3/2001 | Haller et al. |
| 6,210,345 | B1 | 4/2001 | Van Brunt |
| 6,210,347 | B1 | 4/2001 | Forsell |
| 6,221,024 | B1 | 4/2001 | Miesel |
| 6,224,857 | B1 | 5/2001 | Romeo et al. |
| 6,306,088 | B1 | 10/2001 | Krausman et al. |
| 6,327,503 | B1 | 12/2001 | Familoni |
| 6,371,965 | B2 | 4/2002 | Gifford, III et al. |
| 6,372,494 | B1 | 4/2002 | Naughton et al. |
| 6,383,218 | B1 | 5/2002 | Sourdile et al. |
| 6,383,219 | B1 | 5/2002 | Telandro et al. |
| 6,387,105 | B1 | 5/2002 | Gifford, III et al. |
| 6,417,750 | B1 | 7/2002 | Shon |
| 6,418,934 | B1 | 7/2002 | Chin |
| 6,419,696 | B1 | 7/2002 | Ortiz et al. |
| 6,432,040 | B1 | 8/2002 | Meah |
| 6,439,539 | B1 | 8/2002 | Powell |
| 6,443,957 | B1 | 9/2002 | Addis |
| 6,443,965 | B1 | 9/2002 | Gifford, III et al. |
| 6,450,173 | B1 | 9/2002 | Forsell |
| 6,450,946 | B1 | 9/2002 | Forsell |

(56) References Cited

U.S. PATENT DOCUMENTS

| | | |
|---|---|---|
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 | 4/2003 | Dargent et al. |
| 6,565,582 B2 | 5/2003 | Gifford, III et al. |
| 6,578,239 B2 * | 6/2003 | Hatch .................. 24/16 PB |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fisher et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 * | 2/2007 | Hofle et al. .................. 606/151 |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrun |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 * | 11/2010 | Benchetrit .................. 606/157 |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Caseres et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 * | 3/2004 | Benchetrit .................. 606/151 |
| 2004/0059393 A1 | 3/2004 | Policker et al. |
| 2004/0068847 A1 | 4/2004 | Belisle et al. |

(56) References Cited

U.S. PATENT DOCUMENTS

| | | |
|---|---|---|
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0082793 A1 | 4/2005 | Lee |
| 2005/0100779 A1 | 5/2005 | Gertner |
| 2005/0104457 A1 | 5/2005 | Jordan et al. |
| 2005/0119672 A1* | 6/2005 | Benchetrit ............ 606/151 |
| 2005/0119674 A1 | 6/2005 | Gingras |
| 2005/0131383 A1 | 6/2005 | Chen et al. |
| 2005/0131485 A1 | 6/2005 | Krundson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0227936 A1 | 10/2005 | McSwiggen |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neil |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |

(56) References Cited

U.S. PATENT DOCUMENTS

| | | |
|---|---|---|
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0201874 A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 A1 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2095796 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |

(56) References Cited

FOREIGN PATENT DOCUMENTS

| | | |
|---|---|---|
| WO | WO 01/85071 | 11/2001 |
| WO | WO 02/05753 | 1/2002 |
| WO | WO 02/09792 | 2/2002 |
| WO | WO 02/019953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | PCT/US03/26678 | 3/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 7/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.
Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.
Dixon et al.; "Pregnancy After Lap-Band Surgery: Management of the Band to Achieve Healthy Weight Outcomes"; Obesity Surgery; V. 11, pp. 59-65; 2001.
Neary et al.; "Peptide YY(3-36) and Glucagon-Like Peptide-$1_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.

Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Corporation, an Inamed Company, BioEnterics Intragastric Balloon; Directions for Use Published Document, P/N 94200 Rev: B, pp. 1-56, 2001.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and inclipped position"; Interact Cardio Vase Thorac Surg 2002; 1:46-49; Copyright @ 2002 the European Asociation for Cardio-thoracic Surgery; 1 page.
Cummings et al.; "Plasma Ghrelin Levels After Diet-Induced Weight Loss or Gastric Bypass Sugery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.

(56) References Cited

OTHER PUBLICATIONS

Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V. 13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: A Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.
Small et al.; "Gut hormones and the control of appetite"; TRENDS in Endocrinology and Metabolism; V. 15. No. 6; pp. 259-263; Aug. 2004.
Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptidel secretion"; J. Physiol.; V. 587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinal Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

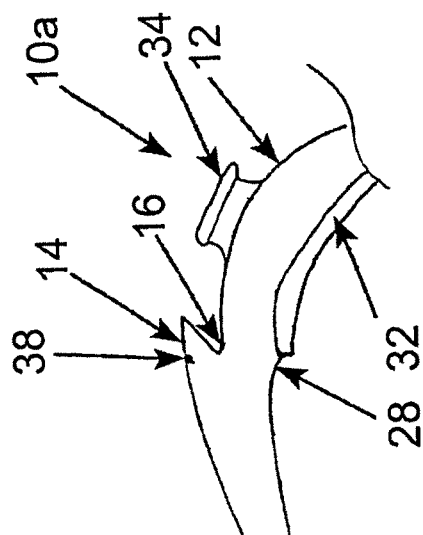
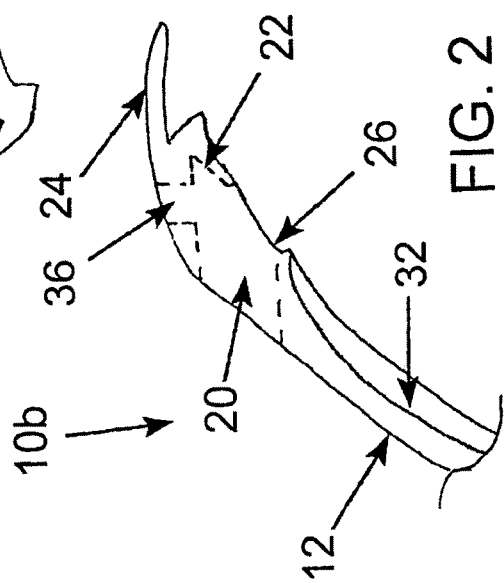

RELEASABLY-SECURABLE ONE-PIECE ADJUSTABLE GASTRIC BAND

BACKGROUND OF THE INVENTION

1. Field of the Invention

The present invention relates generally to surgically implanted gastric bands for encircling the stomach having a releasable securing appendage. A method for treating morbid obesity utilizing a releasably-securable gastric banding device is also disclosed.

2. Description of the Related Art

A belt-like gastric band for encircling the stomach to control morbid obesity is disclosed by Vincent in U.S. Pat. No. 5,601,604, incorporated herein by reference. The band comprises a belt that can be passed around the stomach and locked into an encircling position in order to create a stoma opening within the stomach. An adjustable portion of the band comprises an inflatable member, which permits fine adjustment of the stoma opening after the stoma is created by locking the band in place. The stoma opening may be adjusted by adding or withdrawing a fluid into or from an inflatable member. The means for injecting the fluid into the inflatable member usually comprises a fill port located beneath the skin that can be accessed extracorporeally by transdermal injection. Thus, following implantation, the gastric band can be adjusted to enlarge or reduce the stoma as required.

The gastric band is implanted surgically, via laparoscopy or laparotomy, and may involve placement of a calibrating apparatus in the stomach to position the stoma and size the pouch created above the stoma. The gastric band is imbricated in position about the stomach to prevent slippage, usually by gastro-gastric sutures (i.e. tissue is wrapped over the band and sutured to itself).

As disclosed by Vincent, the inflatable member or shell is preferably substantially coextensive with an inner stomach-facing surface of the gastric band. Furthermore, it has been observed that the inflatable member should not wrinkle or fold when adjusted, so as to present a substantially smooth contour along the inner circumference. This ensures not only that stomach tissue will not be pinched by the inflatable member, which could lead to discomfort or necrosis, but also protects the shell from a phenomenon known as crease fold failure, which may occur if it is inflated beyond its intended range of adjustment or if the shell is not formed in a toroidal or circular shape.

In use, it has been observed that current gastric bands cannot be easily released once they are locked in place around the stomach to form the stoma. This can be a significant setback for a surgeon attempting to move a gastric band after implantation. In particular, a patients' physiology or change in physiology may necessitate moving the band after initial placement. Other factors that could require moving or releasing the band include a patient's inability to control food intake.

In instances where the band has slid out of place, is improperly placed, or where changes in patient physiology require movement of the band, the currently known gastric bands do not provide for releasing the locking means that hold the band securely around a patient's stomach. While some devices may ultimately be releasable, such devices typically require exertion of considerable force, which can cause damage to or failure of the band. Further, when manipulating the band laparoscopically, the amount of force that can be applied during such a procedure is very limited.

One gastric banding device that appears to have some ability to be locked and unlocked has been marketed under the name HELIOGAST®. The Heliogast band is an inflatable gastric band having an inflatable locking means attached to the tail and which is inserted into a loop attached to the head of the band. After implantation, the band must be inflated to lock the band in place. In theory, this band could be re-opened after placement to allow a medical professional to reposition the band. However, it suffers from the drawback that it must be inflated to lock into position and therefore it must be deflated before being opened and moved. The requirement that the band must be inflated to lock also limits the range of the stoma opening that can be achieved by such a band, as the band must necessarily have a certain amount of liquid pressure inside the band in order to lock. Consequently, the range of adjustment of the Heliogast band is limited in comparison with the band of the present invention, which can be locked regardless of its inflation level. In addition the band can be opened by application of a smaller force than those of the prior art. The smaller force's ability to overcome the locking mechanism increases the possibility of the band unlocking accidentally, such as during vomiting by the patient.

Accordingly, there is a need for a releasable gastric band that can be releasably locked in place around a patient's stomach, released or unlocked to reposition the gastric band on the patient's stomach (or remove the band altogether), and then secured in place again around the patient's stomach. There is further a need for a releasably-securable gastric band that does not require deflation before being released, and which may be locked in place without subsequent inflation of the locking means. Additionally, there is a need for a gastric band that resists being unlocked by normal physiological forces There is also a need for an adjustable gastric band with increased ease of use when compared to those currently on the international market, specifically a gastric band that has high tensile force resistance along the band, while being able to be opened with reduced force.

Various other objects, advantages and features of the present invention will become readily apparent from the ensuing description and the novel features will be particularly pointed out in the appended claims.

SUMMARY OF THE INVENTION

The present invention is directed to a releasably-securable inflatable gastric band having a tail end and a head end for receiving the tail end. The gastric band also includes a releasable locking means that releasably secures the head and tail ends together. The tail end may include a tooth and the head end may include a notch for engaging the tooth. Upon insertion of the tail end into the head end, the tooth mates with the notch and releasably locks the tail end in the head end. The releasably-securable gastric band may also include a release tab. When force is applied to the release tab in a direction perpendicular to a central axis of the gastric band, the release tab acts on the tooth and the tooth is moved from the notch. This movement of the tooth from the notch allows the gastric band to open.

The various features of novelty that characterize the invention are pointed out in particularity in the claims annexed to and forming a part of this disclosure. For a better understanding of the invention, its operating advantages and specific objects attained by its uses, reference is made to the accompanying descriptive matter in which preferred embodiments of the invention are illustrated.

BRIEF DESCRIPTION OF THE DRAWINGS

FIG. 1 is a side view of a tail end of a gastric band according to the present invention;

FIG. 2 is a side view of a head end of a gastric band according to the present invention;

DETAILED DESCRIPTION

The present invention is directed to a laparoscopic implantable adjustable gastric band designed to be opened or released laparoscopically in order to facilitate repositioning or removal when necessary. Once locked in position, previously known laparoscopic gastric bands, such as the LAP-BAND®, can only be opened with difficulty and at the risk of damaging the components due to the force required. While particularly suited to laparoscopic implantation, release and/or removal, the gastric band of the present invention is also suitable for standard laparotomy procedures.

Figure 6:
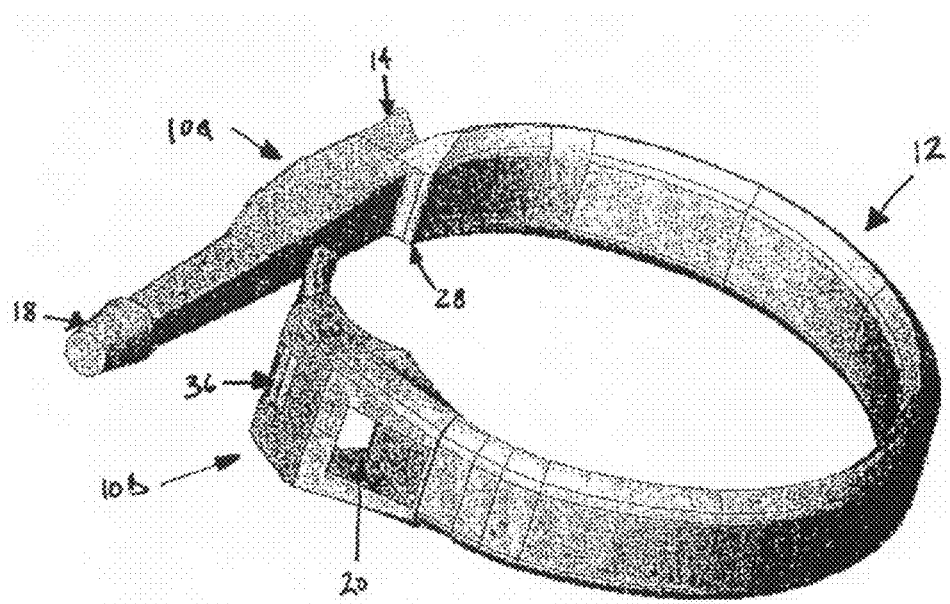
FIG. 6 is a perspective view of a gastric band according to the present invention showing the head end in the foreground.
Figure 7:
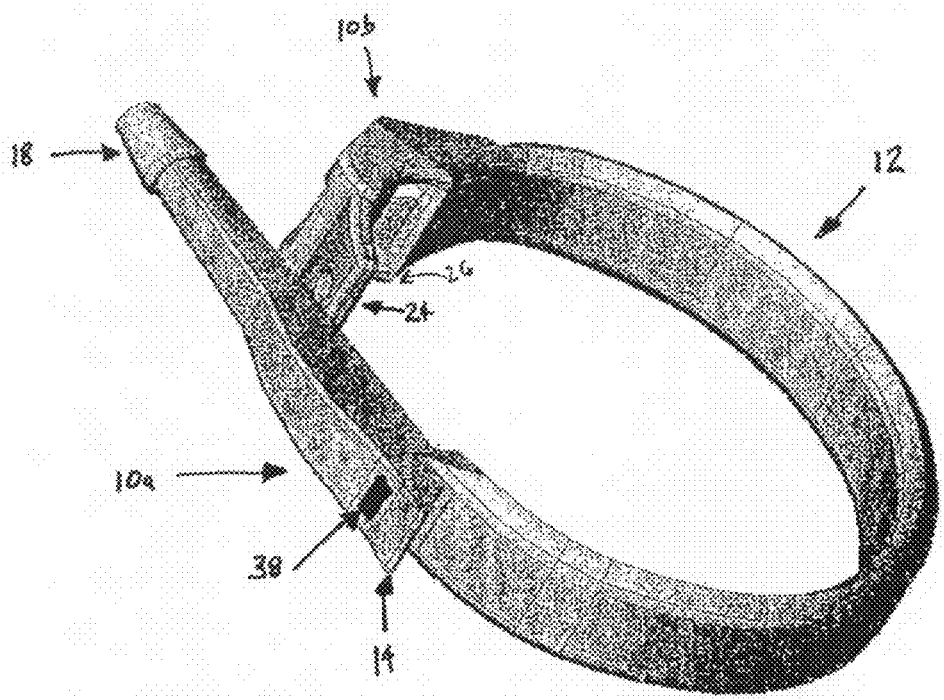
FIG. 7 is a perspective view of a gastric band according to the present invention showing the tail end in the foreground.

Turning now to FIGS. 1 and 7, there is shown a tail end 10a of a releasably-securable gastric band 12. In FIGS. 2 and 6, the head end 10b of gastric band 12 is depicted. The tail end 10a comprises a elongated tip 18, which may incorporate an inflation tube 30, and a sloped tooth 14. Inflation tube 30 has a lumen therethrough to allow fluid to be added to or removed from the an inflatable portion of the band 32 to hydraulically adjust the diameter of the band when it is in an encircling position about the stomach or desired organ. As is well known in the art, a stoma of desired size may be by created by adjusting the diameter of the gastric band. The adjustment may be carried out hydraulically or mechanically. In a hydraulically-adjustable gastric band, inflation tube 30 need not be incorporated into tail end 10a. Instead, it may be incorporated at head end 10b or at any point in between. Alternatively, gastric band 12 may be adjusted through a variety of known mechanical means. Whether hydraulic or mechanical, gastric band 12 is preferably adjusted via remote control from outside the body. Such remote adjustable restriction devices may be active devices, i.e. powered by implantable sources of energy such as batteries, capacitors, etc. or passive devices powered from outside the body by energy transferred through radio frequency, induction, electromagnetic energy, etc.

Turning back to the releasably locking features of the present invention, tooth 14 is defined on one side by a notch 16, and may include a visual indicator 38, which will be discussed below in conjunction with the head end 10b. Also shown in FIG. 1 is the adjustable portion of the band 32. Formed on the head end 10a of the gastric band 12 is a gripping land 34, which allows the surgeon or other medical professional to grip the gastric band 12 without fear of damaging the fluid bearing portions of the band. The gripping land 34 is especially helpful when releasing a previously locked gastric band.

The head end 10b, as shown in FIG. 2, includes a buckle 20 that receives and locks the tail end 10a to form the band in an encircling position about the stomach. The buckle 20 has an aperture, or opening, that allows a part of the tail end 10a to be drawn through the buckle 20. The buckle 20 includes a notch 22 for receiving the tooth 14 of the tail end 10a. The head end 10b further comprises a release tab 24. Another aspect of the head end 10b is the indicator window 36, which allows the surgeon or other medical professional to view the indictor 38 portion of the tail end 10a, preferably enhanced by a contrasting color or texture, when inserted into the head end 10b to provide positive visual and/or tactile indication that the gastric band had been releasably locked in position.

In practice, the gastric band is implanted around the stomach of the patient using now-standard laparoscopic or laparotomic procedures well known by those of skill in the gastric banding art. Once the gastric band 12 encircles the stomach and is positioned in the desired location along the length of the stomach, the tail end 10a is inserted into the buckle 20 of the head end 10b. A closure tool, such as that described in U.S. Pat. No. 5,658,298 to Vincent and Coe, the disclosure of which is incorporated herein by reference, may be used to secure the tail and head ends, 10a and 10b respectively, together. For example, the tail end 10a is drawn through the buckle 20 until the tooth 14 and the notch 22 engage or interlock and prevent the gastric band 12 from opening. When the two ends of the gastric band are properly locked together, the indicator 38 on the tail end 10a is visible through window 36 on the head end 10b. The buckle 20 of the head end 10b encircles, or surrounds, the tail end 10a. The part of the tail end 10a that is drawn through and exits the buckle 20 may be identified as a first part of the tail end 10a, and the part of the tail end 10a remaining within the buckle 20 when the gastric band 12 is releasably secured may be identified as a second part of the tail end 10a.

Further elements of the gastric band 12 are the mating recesses 26 and 28 of the head and tail ends 10a and 10b respectively. These recesses, which are substantially the negative image of one another, butt together and prevent the overlap of the two ends of the inner stomach-facing surface 32 of the gastric band when the band is in its closed position. The recesses 26 and 28 are formed on the head and tail ends respectively to ensure a substantially smooth continuous surface contacts the patient's stomach.

The releasably-securable gastric band according to the present invention requires a two-step procedure to release its locking head and tail ends. First the interlocking tooth 14 and notch 20 are disengaged by pulling on the release tab 24 in a direction substantially perpendicular to a central axis of the now-closed gastric band 12. To assist in pulling on the release tab 24, the surgeon or other medical professional may also grasp the gripping land 34 with a second medical instrument. Doing so helps hold the gastric band 12 in place so that force can be efficiently applied to the release tab 24. Next, the tail 10a may be removed from the head end 10b if the band is to be removed or loosened sufficiently to allow the gastric band 12 to be repositioned along the length of the patient's stomach.

Through the use of a slightly elongated head end 10b, as compared to the LAP-BAND® of the prior art and U.S. Pat. No. 5,601,604, pulling on the release tab 24 causes a translational force toward the central axis of the gastric band 12, thereby unlocking and releasing the head and tail ends of the gastric band 12 of the present invention to permit repositioning or removal of the gastric band 12 without fear of damaging the gastric band. Both the fit of the tooth 14 and recess 20, and the elasticity of the materials from which the gastric band are made can be optimized to ensure a sufficiently secure closure of the gastric band that requires relatively little force on the release tab 24 to open.

Naturally, geometries other than the tooth 14 and notch 22 may be used to achieve the ability to releasably secure the band in accordance with the present invention. One such geometry includes multiple smaller interlocking elements. Further, the locking elements could be shaped for a "pop-fit" to provide tactile indication that the band is secured in place or if greater resistance to disengagement is desired.

Figure 3:
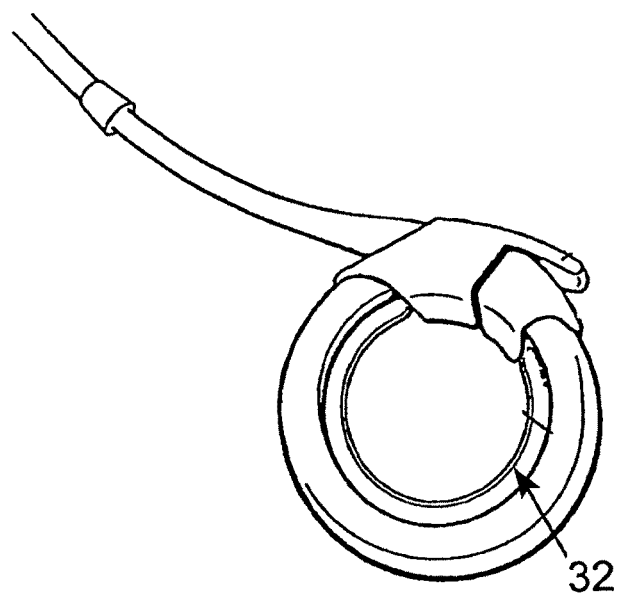
FIG. 3 depicts a gastric band according to the present invention having a smooth inflatable member.
Figure 4:
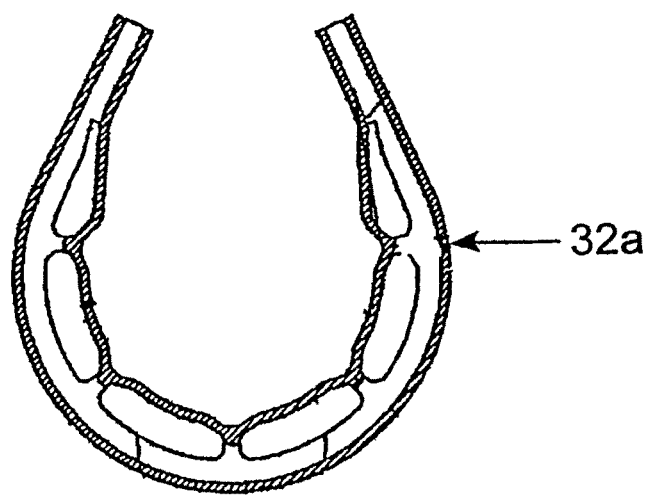
FIG. 4 depicts a fatigue resistant inflatable member of a gastric band.
Figure 5:
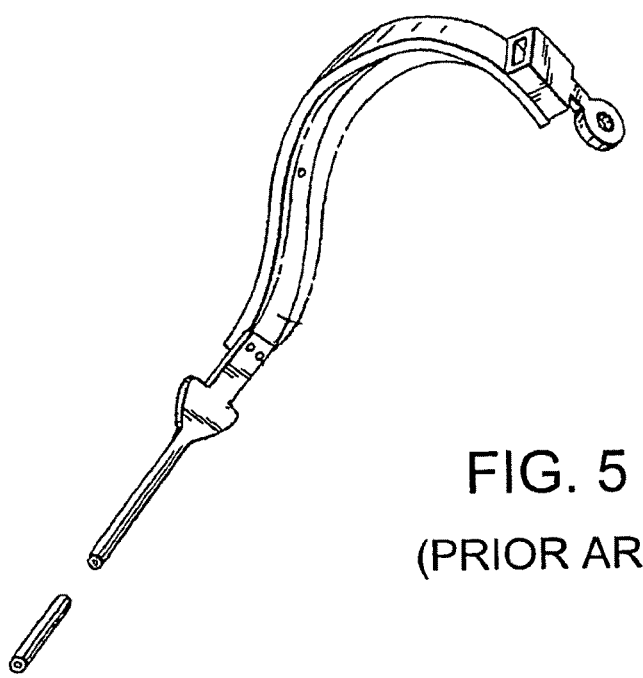
FIG. 5 depicts a prior art gastric band according to U.S. Pat. No. 5,601,604 to Vincent.

The present invention may be used in conjunction with a substantially smooth adjustable member 32, as shown in FIG. 3, and known in the art. Alternatively, the present invention may be used in conjunction with a newer fatigue-resistant inflatable member 32a, as shown in FIG. 4. A fatigue resistant band is described in detail in PCT/US03/26678 and is incorporated herein by reference. As described therein, the fatigue resistant inflatable portion 32a is multi-chambered and resistant to wrinkling or folding over its range of adjustment. Like the adjustable portion 32 shown in FIG. 3, the fatigue resistant inflatable portion 32a presents a substantially smooth contour along the inner circumference to promote the comfort of the wearer and avoid pinching of the stomach that can lead to necrosis. The fatigue resistant inflatable member is shown in cross-section in FIG. 4 separate from a complete gastric band to better illustrate its novel features. As with previous bands, a gastric band comprising a fatigue resistant inflatable portion 32a can be preformed in a circle, can be locked in place by the surgeon or medical professional, and in one preferred embodiment is inflated via an inflation lumen running through the tail end 10a of the gastric band.

Gastric bands according to the present invention may be constructed in sequential molding steps, resulting in a fully automated assembly and a high degree of precision. Further, the materials from which the gastric band may be made include silicone and other materials known to those of skill in the art as compatible for implantation within the body.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

What is claim is:

1. A releasably-securable adjustable gastric band for the treatment of obesity suitable for laparoscopic placement around the stomach of a patient, and suitable for laparoscopic removal from said stomach, comprising:
    an inflatable portion;
    a tail end connected to the inflatable portion;
    a head end, connected to the inflatable portion, having an aperture structured to allow a first part of said tail end to be drawn through said aperture to position a second part of said tail end within said head end such that said head end encircles said second part of said tail end;
    a releasable locking means including a tooth and a notch structured to engage said tooth to releasably secure said head end to said tail end when said first part of said tail end is drawn through said aperture, to thereby releasably secure said releasably-securable adjustable gastric band in an encircling position around said patient's stomach;
    a visual securing indicator of a contrasting color or texture;
    a window through which the visual securing indicator is visible to provide positive visual indication when said head end and said tail end are releasably secured together; and
    a release tab positioned on said head end and structured to allow said releasable locking means to release said tail end from said head end when a force is applied to said release tab.

2. The releasably-securable gastric band of claim 1, wherein said tooth is formed on a portion of said tail end.

3. The releasably-securable gastric band of claim 2, wherein said notch is in said head end.

4. The releasably-securable gastric band of claim 1, wherein application of said force to said release tab in a direction substantially perpendicular to a central axis of said releasably-securable adjustable gastric band allows said tooth to disengage from said notch so as to allow the release of said tail end from said head end.

5. The releasably-securable gastric band of claim 1, further comprising a tactile securing indicator.

6. The releasably-securable gastric band of claim 1, wherein said releasably-securable adjustable gastric band is adjustable via hydraulic inflation.

7. The releasably-securable gastric band of claim 6, further comprising an inflation tube.

8. The releasably-securable gastric band of claim 7, wherein said tail end comprises said inflation tube.

9. The releasably-securable gastric band of claim 7, wherein said head end comprises said inflation tube.

10. The releasably-securable gastric band of claim 1, wherein said releasably-securable adjustable gastric band is mechanically adjustable.

11. The releasably-securable gastric band of claim 1, wherein said releasably-securable adjustable gastric band is remotely adjustable.

12. The releasably-securable gastric band of claim 1, wherein application of said force to said release tab lifts said notch over said tooth to allow the release of said tail end from said head end.

13. The releasably-securable gastric band of claim 1, wherein an inflation tube comprises said second part of said tail end.

14. The releasably-securable gastric band of claim 1, wherein the position of the visual indicator corresponds to the position of only one tooth.

15. The releasably-securable gastric band of claim 14, wherein said releasably-securable adjustable gastric band is releasably locked in place when said visual securing indicator appears in said window following insertion of said tail end into said head end.

16. The releasably-securable gastric band of claim 1, wherein the appearance of the visual indicator through the window corresponds to only the position of the notch engaged relative to the tooth.

17. The releasably-securable gastric band of claim 1, wherein the release tab is constructed to release the tail end from the head end when the force is applied in a direction substantially perpendicular to a central axis of the gastric band.

* * * * *